United States Patent
Rodriguez

(10) Patent No.: US 9,163,240 B2
(45) Date of Patent: Oct. 20, 2015

(54) SR-BI MUTATION AS A PREDICTOR OF LOW PROGESTERONE LEVELS AND POOR FETAL VIABILITY DURING PREGNANCY

(75) Inventor: Annabelle Rodriguez, Cockeysville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/514,392

(22) PCT Filed: Dec. 7, 2010

(86) PCT No.: PCT/US2010/059274
§ 371 (c)(1),
(2), (4) Date: Jun. 7, 2012

(87) PCT Pub. No.: WO2011/071916
PCT Pub. Date: Jun. 16, 2011

(65) Prior Publication Data
US 2013/0034539 A1    Feb. 7, 2013

Related U.S. Application Data

(60) Provisional application No. 61/261,412, filed on Dec. 7, 2009, provisional application No. 61/378,083, filed on Aug. 30, 2010.

(51) Int. Cl.
| | | |
|---|---|---|
| *C12Q 1/68* | (2006.01) | |
| *C07H 21/02* | (2006.01) | |
| *A61K 31/57* | (2006.01) | |
| *C07H 21/04* | (2006.01) | |
| *C12N 15/113* | (2010.01) | |
| *A61K 38/00* | (2006.01) | |

(52) U.S. Cl.
CPC .......... *C12N 15/1138* (2013.01); *C12Q 1/6883* (2013.01); *A61K 38/00* (2013.01); *C12N 2310/14* (2013.01); *C12Q 2600/156* (2013.01)

(58) Field of Classification Search
CPC ................. C12Q 2600/156; C12Q 2600/172; C12Q 2600/118; C12Q 1/6827; C12Q 1/6883
See application file for complete search history.

(56) References Cited

U.S. PATENT DOCUMENTS

| | | | |
|---|---|---|---|
| 6,228,581 B1 * | 5/2001 | Acton et al. ................. | 435/6.11 |
| 2003/0232879 A1 | 12/2003 | Krieger et al. | |
| 2004/0171073 A1 | 9/2004 | Neiland et al. | |
| 2009/0324580 A1 * | 12/2009 | Hannus et al. ............. | 424/130.1 |

FOREIGN PATENT DOCUMENTS

| | | | |
|---|---|---|---|
| WO | 2009/097418 A2 | | 8/2009 |
| WO | WO 2009/097418 | * | 8/2009 |

OTHER PUBLICATIONS

GeneCard for SR-BI / SCARB1 available via url: < genecards.org/cgi-bin/carddisp.pl?gene=SCARB1>, printed on Oct. 28, 2013.*
Gagneux et al Molecular Phylogenetics and Evolution. 2001. 18: 2-13.*
Halushka et al. Nature. Jul. 1999. 22: 239-247.*
Mummidi et al. Journal of Biological Chemistry 2000 vol. 275 No. 25 pp. 18946-18961.*
Hirschhorn et al. Genetics in Medicine. 2002. 4(2): 45-61.*
Hattersley et al. The Lancet. 2005. 366: 1315-1323.*
Lucentini et al. The Scientist (2004) vol. 18, p. 20.*
NCBI SNP Database, National Center for Biotechnology Information, National Library of Medicine (Bethesda, MD, USA) Reference SNP Cluster Report for rs4238001, printed on Nov. 12, 2014.*
Trigatti, B., et al., "The role of the high-density lipoprotein receptor SR-BI in cholesterol metabolism" Current Opinion in Lipidology, 11: 123-131 (2000).
West, M., et al., "Scavenger receptor class B type I protein as an independent predictor of high-density lipoprotein cholesterol levels in subjects with hyperalphalipoproteinemia" J. Clin. Endocrinol. Metab., 94: 1451-1457 (Apr. 2009).

* cited by examiner

*Primary Examiner* — Carla Myers
(74) *Attorney, Agent, or Firm* — Johns Hopkins Technology Transfer

(57) ABSTRACT

Methods of diagnosis and treatment of diseases and disorders related to de novo synthesis of cholesterol, based on allelic variants of the scavenger receptor class B type I receptor, and kits for use therein.

2 Claims, 10 Drawing Sheets

*p<0.01 COMPARED WITH SCRAMBLED

- ◆ DMSO
- ■ FORSKOLIN
- ▲ FORSKOLIN+LDL
- ● LDL

TIME (h)

MEDIA PROGESTERONE (ng/mg CELL PROTEIN)

*$p<0.001$ AND **$p<0.01$ COMPARED TO SCRAMBLED CONDITIONS p<0.01 MEAN CHANGE COMPARED TO SCRAMBLED

*p<0.001 FOR MEAN CHANGE OF PROGESTERONE AS COMPARED TO SCRAMBLED

*p<0.01 COMPARED WITH SCRAMBLED

*p<0.01 FOR MEAN COMPARED WITH THE SCRAMBLED CONTROL

ASSOCIATION OF SCARB1 SNPs WITH FOLLICULAR PROGESTERONE LEVELs: ENTIRE COHORT

*p<0.08 COMPARED WITH HOMOZYGOUS G ALLELE; **p=0.03 COMPARED WITH HOMOZYGOUS MAJOR C ALLELE

SR-BI MUTATION AS A PREDICTOR OF LOW PROGESTERONE LEVELS AND POOR FETAL VIABILITY DURING PREGNANCY

CROSS-REFERENCE TO RELATED APPLICATIONS

This application is a 35 U.S.C. §371 U.S. national entry of International Application PCT/US2010/059274 having an international filing date of Dec. 7, 2010, which claims the benefit of U.S. Provisional Application No. 61/378,083, filed Aug. 30, 2010, and, U.S. Provisional Application No. 61/261,412, filed Dec. 7, 2009, the contents of each of the aforementioned applications are herein incorporated by reference in their entireties.

FIELD OF THE INVENTION

The invention relates to methods of diagnosis and treatment of diseases and disorders related to de novo synthesis of cholesterol, based on allelic variants of the scavenger receptor class B type I receptor.

BACKGROUND

Deficiency of the lipoprotein receptor, scavenger receptor class B type I receptor (SR-BI), might possibly explain, at least in part, some aspects of infertility in humans. SR-BI is a physiologically relevant lipoprotein receptor that mediates the uptake of cholesteryl esters (CE) from the core of lipoproteins (1). SR-BI has also been shown to colocalize in the perinuclear region of cells, with as yet an undefined function (2). It has been shown to be highly expressed in liver and steroidogenic tissues, with particularly high levels found in ovarian tissues (3). SR-BI deficiency is significantly associated with infertility in female mice (4). These female knock-out mice have been shown to ovulate dysfunctional oocytes and embryogenesis is abnormal (5). Interestingly, fertility can be restored with either the addition of probucol, a cholesterol lowering antioxidant drug (3) in the chow diet, or by genetically restoring liver SR-BI protein expression (6).

Little is known regarding the role of SR-BI in human fertility. The present inventor with collaborators was the first to show that infertile women with low expression of SR-BI RNA in granulosa cells isolated during oocyte retrievals had significantly lower plasma estradiol levels and lower number of retrieved and fertilized oocytes (7). Other evidence for the role of SR-BI on aspects of ovarian steroidogenesis has been based on the results of ex vivo studies in non-human primates and rat granulosa cells. For instance, Cherian-Shaw reported that SR-BI RNA levels increased steadily by ~30-fold in macaque granulosa cells 24 h after stimulation by human chorionic gonadotropin (hCG), whereas LDL receptor expression initially increased but then decreased to low basal levels during this early time period (8). Earlier work by Azhar et al. (9) showed that induction of SR-BI expression in rat granulosa cells was significantly associated with increased CE uptake from HDL and with increased total progestin secretion. These investigators subsequently showed that LDL receptor deficiency had minimal effect on murine ovarian progesterone secretion (10).

One goal of the present investigation was to define the effect of SR-BI protein deficiency on progesterone secretion in cultured human granulosa HGL5 cells, with confirmatory findings in primary human granulosa cells isolated during oocyte retrievals. In agreement with other investigators, the present inventor and her collaborators have found that LDL is the preferential lipoprotein supporting steroidogenesis (11, 12,13,14). SR-BI, in contrast to the LDL receptor (LDLR), appears to have a major effect on progesterone secretion. Deficiency of SR-BI significantly reduced RNA expression of p450 side-chain cleavage (SCC), 3β-hydroxysteroid dehydrogenase (3βHSD), and steroidogenic acute regulatory protein (StAR).

SUMMARY

One aspect of the invention is the discovery that SR-BI plays a role in de novo cholesterol synthesis. It is expected that this knowledge will enable the treatment of disorders that rely on de novo cholesterol synthesis to develop, such as disorders of cell growth, e.g. cancer in tissues expressing SR-BI, such as ovarian cancer, disorders of neovascularization such as diabetic retinopathy, and age-related macular degeneration. Accordingly, SR-BI is a useful target for inhibition and treatment of such diseases. Inhibition of SR-BI can be accomplished by any method known in the art, including antibodies, antisense oligonucleotides, antisense constructs, RNA interference constructs, siRNA duplex RNA molecules, microRNA, or small chemical molecules. Inhibitors of downstream events in the de novo cholesterol pathway can also be used.

More particularly, methods are provided for using the presence of particular SNPs in the SR-BI gene to diagnose or prognosticate regarding susceptibility of a subject for developing a particular disorder or condition. For example, the present invention relates to methods for identifying subjects at risk for infertility or poor fetal viability during pregnancy. The present invention may also be used to identify subjects at risk for developing disorders of cell growth and neovascularization as mentioned above. The presence of particular SNPs result in a change in the amino acid sequence of the SR-BI protein, which in turn leads to lower amounts of the protein being made by cells. Certain SNPs in the SR-BI gene correlate to a risk, elevated risk, an increased probability, and/or otherwise a predisposition to develop a particular condition, disease or disorder. In one embodiment, specific SNPs are expected to correlate with development of diseases of neovascularization such as cancer in tissues expressing SR-BI (e.g. ovarian cancer, adrenal adenomas, adrenal carcinomas, hepatocellular carcinomas, diabetic retinopathy, age related macular degeneration, retinoblastomas).

In certain embodiments, specific SNPs of the SR-BI gene lead to a decreased level of progesterone which in turn, may lead to problems in fertility or during pregnancy, recurrent spontaneous miscarriages, and/or increased risk for ovarian cancer. When such subjects are identified, early intervention and improved outcome may be possible.

Accordingly, polymorphic changes to the SR-BI gene, which lead to an altered form and level of the SR-BI protein may be useful to identify subjects at risk, with an elevated risk, with an increased probability, and/or otherwise a predisposition for a variety of conditions. The methods and kits of the present invention are further described in more detail below.

In one embodiment, methods are provided to predict or diagnose infertility in women. For example, the presence of certain SNPs of SR-BI in an individual may help identify the underlying cause of infertility.

The present invention provides methods and kits for identifying subjects at risk for, or identifying and/or treating subjects afflicted with a particular disease or condition. In one embodiment, the condition is low fertility or poor fetal viability in a human female, resulting in poor pregnancy outcomes.

In other embodiments, the disease is a disorder of cell growth, e.g. cancer in tissues expressing SR-BI, such as ovarian cancer (see above), disorders of neovascularization such as diabetic retinopathy and age-related macular degeneration.

In one embodiment, the methods and kits of the present invention are directed to identifying in subjects the presence of one or more allelic variants in the SR-BI gene. The allelic variant may comprise a polymorphic region of the SR-BI gene. In particular embodiments, the polymorphism may comprise one or more single nucleotide polymorphisms or SNPs. Accordingly, the present invention provides methods and kits directed to identifying the presence of one or more SNPs within the SR-BI gene of a subject, thereby predicting risk or diagnosing a disease or condition associated with the SNP.

In one embodiment, a method of prognosticating low progesterone levels and/or poor fetal viability during pregnancy in a female subject is provided, the method comprising the step of screening a biological sample from the subject for the presence of a single nucleotide polymorphism (SNP) in the SR-BI gene, wherein the presence of the SNP indicates an elevated risk of low progesterone levels and/or poor fetal viability in the subject. In particular, the presence of SNP rs4238001 is considered to be correlated with low progesterone levels and/or poor fetal viability.

Also provided is a method for determining whether a human female subject is at increased risk for having or developing low fertility, infertility or decreased fetal viability during pregnancy comprising the step of screening a biological sample from the human subject for the presence of a SNP in the SR-BI gene, wherein the presence of the SNP indicates that the subject is at increased risk of low fertility, infertility or decreased fetal viability. For example, a method can comprise the step of screening a biological sample from a subject for the presence of a SNP in the SR-BI gene, wherein the presence of the SNP increases the risk of the subject having or developing low fertility, infertility or decreased fetal viability by at least 10% preferably at least 25%, 50%, 75%, 90%, 95% or 99% relative to a subject in which such SNP is absent from the SR-BI gene. In an alternative embodiment, the method can comprise the step of screening a biological sample from a subject for the presence of a SNP in the SR-BI gene, wherein the presence of the SNP increases the risk of the subject developing a low fertility, infertility or decreased fetal viability by at least about 10% to at least about 50% relative to a subject in which such SNP is absent from the SR-BI gene. The SNP can be selected from group consisting of rs4238001, rs10846744, rs2278986, rs5891, and rs5888.

The present invention also provides kits for carrying out the methods disclosed herein. In one embodiment, the present invention provides a kit for screening for an elevated risk of low fertility, infertility or decreased fetal viability in a subject comprising (a) material for identifying the presence of a SNP in the SR-BI gene of the subject, wherein the presence of such SNP indicates an elevated risk of low fertility infertility or decreased fetal viability in the subject; (b) suitable packaging material; and optionally (c) instructional material for use of the kit.

In other embodiments the kit may screen for an elevated risk of a disease or disorder relating to neovascularization and/or cell proliferation, and contain material for identifying the presence of a SNP in the SR-BI gene of the subject, wherein the presence of such SNP indicates an elevated risk of one or more of these conditions, e.g. cancer, such as ovarian cancer, diabetic retinopathy or macular degeneration.

In the kits for carrying out the method, the material may comprise at least one nucleic acid that specifically binds to a sequence selected from the group consisting of rs4238001, rs10846744, rs2278986, rs5891, and rs5888. The kits may further comprise material to process a nucleic acid-comprising biological sample.

It is understood that the invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. Any and all references to a SNP by the "rs" designation, for example rs4238001 hereby incorporates the associated nucleotide sequence which is easily retrievable by known methods.

This application claims priority to U.S. provisional applications No. 61/261,412, filed Dec. 7, 2009 and 61/378,083, filed Aug. 30, 2010, which are hereby incorporated by reference.

DETAILED DESCRIPTION

Definitions

Figure 1A:
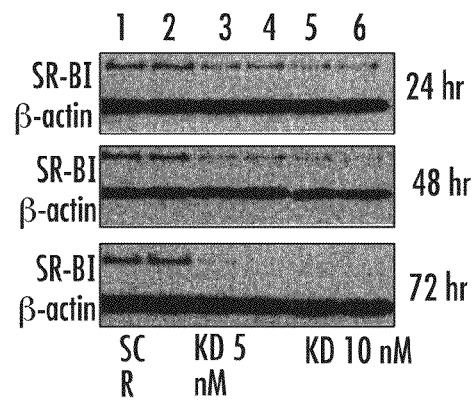
FIG. 1. Effect of HDL and LDL on progesterone secretion in SR-BI knockdown (KD) cells. Panel A: HGL5 cells were seeded at $1.5 \times 10^5$ cells/well in a 12-well format. Scrambled (SCR, lanes 1 and 2) or SR-BI specific siRNA was added (5 nM; lanes 3 and 4, 10 nM; lanes 5 and 6) for 24, 48 and 72 h to knockdown SR-BI protein expression. Levels of SR-BI protein were measured by western blot and normalized to the loading control β-actin. Panel B: Scrambled or SR-BI KD cells were incubated with DMSO or Forskolin (Fo)±HDL (50 µg protein/ml), f LDL (50 µg protein/ml), ±serum (10%), or serum, HDL, and LDL alone for an additional 24 h. The data represent the mean±standard error of three independent experiments, with each experiment performed using duplicate wells. Asterisk denotes p<0.01 between scrambled and SR-BI KD cells.
Figure 1B:
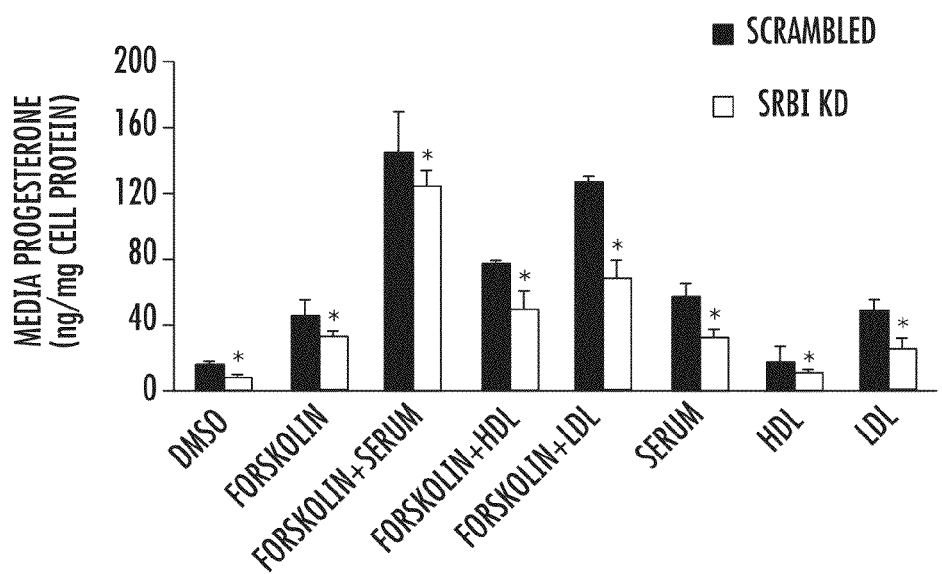

For convenience, the meaning of certain terms, phrases and abbreviations employed in the specification, examples, and appended claims are provided below. The definitions are not meant to be limiting in nature and serve to provide a clearer understanding of certain aspects of the present invention.

As used herein, SR-BI refers to scavenger receptor, class B, type I. The cloning of SR-BI (sometimes referred to as "CLA-1") was first reported by Calvo and Vega in *Identification, Primary Structure, and Distribution of CLA-1, a Novel Member of the CD3/LIMPII Gene Family*, 268(25) J. BIOL. CHEM. 18929-18935 (1993). The human SR-BI gene (also referred to as SCARB1) is at least 50 kilobase pairs long and has 12 coding exons, one non-coding exon (exon 13), and 12 introns. See, e.g., U.S. Pat. No. 6,030,778, which is incorporated herein by reference. The nucleotide sequence of the human SR-BI cDNA encodes a protein of 509 amino acids. As set forth in Calvo and Vega, supra, differential splicing of the human SR-BI gene also results in a short mRNA lacking 300 nucleotides located 126 nucleotides downstream of the initiation codon (lacking exons 2 and 3), and encodes a protein of 409 amino acids. This splice variant is rare relative to the 509 amino acid SR-BI protein.

As used herein, siRNA refers to small interfering RNA.

An "inhibitor" (or "stimulator") of expression or activity is an agent that reduces (or increases) the expression or activity by a detectable amount. An "effective amount" of such an inhibitor (or stimulator) is an amount that is sufficient to elicit a detectable amount of inhibition (or stimulation) of expression, yet does not elicit substantial amounts of undesirable (e.g., toxic) effects.

In one embodiment, the inhibitory molecule is a double stranded nucleic acid (preferably an RNA), used in a method of RNA interference. As used herein, the term siNA (small, or short, interfering nucleic acid) is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. Long double stranded interfering RNAs, such as miRNAs, appear to tolerate mismatches more readily than do short double stranded RNAs. In addition, as used herein, the term RNAi is meant to be equivalent to other terms used to describe sequence specific RNA interference, such as post transcriptional gene silencing, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire (2002) *Science* 297, 1818-1819; Volpe et al. (2002) *Science* 297, 1833-1837; Jenuwein (2002) *Science* 297, 2215-2218; and Hall et al. (2002) *Science* 297, 2232-2237.)

It is well within the ability of a skilled worker to design a sequence-based inhibitor, such as an antisense molecule or an siRNA, that is specific for the SR-BI of any given organism, provided that at least a portion of the sequence encoding the SR-BI is known.

An siNA can be designed to target any region of the coding or non-coding sequence of a gene. An siNA is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary. The siNA can be assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions. The siNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (or can be an siNA molecule that does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al. (2002) *Cell* 110, 563-574 and Schwarz et al. (2002) *Molecular Cell* 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (T-OH) containing nucleotides. In certain embodiments, short interfering nucleic acids do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." Other chemical modifications, e.g., as described in PCT/US03/05346 and PCT/US03/05028, can be applied to any siNA sequence of the invention.

Preferably an RNA interference molecule has a 2 nucleotide 3' overhang. If the RNA interference molecule is expressed in a cell from a construct, for example from a hairpin molecule or from an inverted repeat of the desired SR-BI sequence, then the endogenous cellular machinery will create the overhangs.

Considerations to be taken into account when designing an RNAi molecule include, e.g., the sequence to be targeted, secondary structure of the RNA target and binding of RNA binding proteins. Methods of optimizing siRNA sequences will be evident to the skilled worker. Typical methods are described, e.g., in Vickers et al. (2003) *J Biol Chem* 278, 7108-7118 and Yang et al. (2003) *Proc Natl Acad Sci USA* 99, 9942-9947.

Methods of making siNAs (e.g., siRNAs) are conventional and will be evident to the skilled worker. In vitro methods include, e.g., processing the SR-BI ribopolynucleotide sequence in a cell-free system (e.g., digesting long double strand RNAs with RNAse III or Dicer), transcribing recombinant double stranded SR-BI DNA in vitro, and chemical synthesis of nucleotide sequences homologous to a SR-BI sequence. See, e.g., Tuschl et al. (1999) *Genes & Dev.* 13, 3191-3197. In vivo methods include, e.g., (1) transfecting DNA vectors into a cell such that a substrate is converted into siRNA in vivo [see, e.g., Kawasaki et al. (2003) *Nucleic Acids Res* 31, 700-707; Miyagishi et al. (2003) *Nature Biotechnol* 20, 497-500; Lee et al. (2002) *Nature Biotechnol* 20, 500-505, Brummelkamp et al. (2002) *Science* 296, 550-553; McManus et al. (2002) *RNA* 8, 842-850; Paddison et al. (2002a) *Gene Dev* 16, 948-958; Paddison et al. (2002b) *Proc Natl Acad Sci USA* 99, 1443-1448); Paul et al. (2002) *Nature Biotechnol* 20, 505-508; Sui et al. (2002) *Proc Natl Acad Sci USA* 99, 5515-5520; Yu et al. (2002) *Proc Natl Acad Sci USA* 99, 6047-6052]; (2) expressing short hairpin RNAs from plasmid systems using RNA polymerase III (pol III) promoters [see, e.g., Kawasaki et al. (2003) (supra), Miyagishi et al. (2003) (supra), Lee et al. (2002) (supra), Brummelkamp et al. (2002) (supra), McManus et al. (2002) (supra), Paddison et al. (2002a) (supra), Paddison et al. (2002b) (supra), Paul et al. (2002) (supra), Sui et al. (2002) (supra) and Yu et al. (2002) (supra)]; and/or (3) expressing short RNA from tandem promoters [see, e.g., Miyagishi et al. (2003) (supra) and Lee et al. (2002) (supra)].

When synthesized in vitro, a typical 0.2 micromolar-scale RNA synthesis provides about 1 milligram of siRNA, which is sufficient for about 1000 transfection experiments using a 24-well tissue culture plate format. In general, to inhibit SR-BI expression in cells in culture, one or more siRNAs can be added to cells in culture media, typically to a final concentration of about 50-200 μg, preferably about 50 μg siRNA/ml.

Any of a variety of conventional methods can be used to introduce siNAs into cells, including transfection, electroporation, or other methods known in the art. See, e.g., Hannon (2002) *Nature* 418, 244-251; Bernstein et al. (2002) *RNA* 7, 1509-1521; Hutvagner et al., *Curr. Opin. Genetics & Development* 12, 225-232; Brummelkamp (2002) *Science* 296, 550-553; Lee et al. (2002) *Nature Biotechnol* 20, 500-505; Miyagishi et al. (2002) *Nature Biotechnol.* 20, 497-500; Paddison et al. (2002) *Genes & Dev* 16, 948-958; Paul et al. (2002) *Nature Biotechnol.* 20, 505-508; Sui et al. (2002) *Proc. Natl. Acad. Sci. USA* 99, 5515-5520; and Yu et al. (2002) *Proc. Natl. Acad. Sci. USA* 99, 6047-6052. Nanoparticle methods such as those described by Schiffelers et al.

(2004) *Nucleic Acid Res.* 32:e149 and fusion protein methods such as described by Song et al. (2005) *Nature Biotechnol.* 23:709-717 are also useful.

A skilled worker can readily test a candidate siRNA or antisense variant molecule to determine if it is inhibitory.

For further guidance concerning inhibitory RNAs, see e.g., Lau et al. (2003) *Scientific American, pp.* 34-41; McManus et al. (2002) *Nature Reviews Genetics* 3, 737-747; and Dykxhoorn et al. (2003) *Nature Reviews Molecular Cell Biology* 4, 457-467. For further guidance regarding methods of designing and preparing siRNAs, testing them for efficacy, and using them in methods of RNA interference (both in vitro and in vivo), see, e.g., Allshire (2002) *Science* 297, 1818-1819; Volpe et al. (2002) *Science* 297, 1833-1837; Jenuwein (2002) *Science* 297, 2215-2218; Hall et al. (2002) *Science* 297 2232-2237; Hutvagner et al. (2002) *Science* 297, 2056-60; McManus et al. (2002) *RNA* 8, 842-850; Reinhart et al. (2002) *Gene & Dev.* 16, 1616-1626; Reinhart et al. (2002) *Science* 297, 1831; Fire et al. (1998) *Nature* 391, 806-811, Moss (2001) *Curr Biol* 11, R772-5, Brummelkamp et al. (2002) *Science* 296, 550-3; Bass (2001) *Nature* 411 428-429; and Elbashir et al. (2001) *Nature* 411, 494-498; U.S. Pat. No. 6,506,559; US patent application 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858.

The term "consists essentially of," when used in the context of biopolymers, refers to a sequence which is intermediate between the specific number of residues (amino acids or nucleotides) encompassed by the term "consisting of" and the longer unspecified length encompassed by the term "comprising." Residues in addition to the residues encompassed by "consisting of" language do not affect the basic and novel characteristics (e.g., in the present case, the ability to inhibit SR-BI expression and/or activity) of the molecule encompassed by the "consisting of" language.

For treatment methods disclosed herein, pharmaceutical compositions are normally formulated with a solid or liquid carrier, depending upon the particular mode of administration chosen. The pharmaceutically acceptable carriers useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For example, in addition to injectable fluids, topical and oral formulations can be employed. Topical preparations can include liquids, ointments, sprays and the like. Oral formulations may be liquid (e.g., syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

Effective dosages of the compounds (e.g., inhibitors) of the invention will be evident to the skilled worker. The exact amount (effective dose) of the agent will vary from subject to subject, depending on, i.a., the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents. In general, normal dosage amounts may vary from about 0.1 to 100,000 micrograms, up to a total dose of about 5 g, depending on the nature of the agent, the route of administration and other factors as noted above. For antisense oligonucleotides, the dosage is generally between about 10 mg/kg and about 100 mg/kg, preferably between about 30 mg/kg and about 60 mg/kg. For siRNAs, the dosage is generally between about 1 mg/kg and about 20 mg/kg, preferably between about 5 mg/kg and about 10 mg/kg.

Many suitable routes of administration will be evident to the skilled worker. These include, but are not limited to, oral; respiratory; intranasal; intraorbital; intrarectal; intravaginal; sublingual; intradermal; transdermal; intrethecal; extracorporeal; topical; intravenous, subcutaneous, intramuscular, intramedullary, or intraperitoneal injection; other parenteral routes; or the like. One of skill in the art will recognize particular cells, tissues or organs into which therapeutic agents of the invention can be administered, as appropriate for particular indications.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s), nucleic acid(s) and/or peptide(s) over a period of a few days to months, or even years.

Methods of administering nucleic acids to subjects (patients) are conventional and well known to skilled workers. Such methods include the methods discussed above for introducing nucleic acids, including siRNAs, into cells in culture. Inhibitory nucleic acids of the invention that can be administered to subjects include antisense molecules, ribozymes and siRNAs, as well as recombinant constructs encoding inhibitory nucleic acids or dominant negative cenexins.

Inhibitory nucleic acids can be delivered ex vitro to tumor cells or in vivo to tumors in a mammal. Typical delivery means known in the art can be used. For example, delivery to a tumor can be accomplished by intratumoral injections. Other modes of delivery can be used without limitation, including: intravenous, intramuscular, intraperitoneal, intraarterial, subcutaneous, and per os. In a mouse model, the inhibitory nucleic acid can be administered to a tumor cell in vitro, and the tumor cell can be subsequently administered to the mouse.

Among the methods which have been used successfully to deliver siRNAs are, e.g., plasmid vectors; retrovirus vectors, including oncoretrovirus vectors and lentivirus vectors; and hydrodynamic "high pressure" delivery. When stable expression is desired, particularly in animal models, transgenic animals can be generated.

For the administration of nucleic acids (e.g., methods of gene therapy), a variety of gene delivery vehicles can be used. The gene delivery vehicle may be of viral or non-viral origin (see generally, Jolly, *Cancer Gene Therapy* 1:51-64 (1994) Kimura, *Human Gene Therapy* 5:845-852 (1994); Connelly, *Human Gene Therapy* 1:185-193 (1995); and Kaplitt, *Nature Genetics* 6:148-153 (1994). Gene therapy vehicles for delivery of constructs including a sequence of interest (e.g., a coding sequence or an antisense sequence of the invention) can be administered either locally or systemically. These constructs can utilize viral or non-viral vector approaches. Expression of such sequences can be induced using endogenous mammalian or heterologous promoters. Expression of the sequence can be either constitutive or regulated, e.g., in a tissue-specific or temporally-specific manner.

By "de novo synthesis of cholesterol" is meant newly synthesized cholesterol production by cells or in an animal (mammal, in particular human) body.

By "detecting the presence of" or "detecting an increased (decreased) level of" is meant detecting a statistically significant difference in a substance from the amount detected in a control sample. Examples are detection of an allelic variant in a patient that does not occur in a normal subject, and/or an increased/decreased amount of follicular progesterone in a subject bearing such an allelic variant.

As used herein, the term "allele" or "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation. An allelic variant may comprise one or more single nucleotide polymorphisms ("SNPs").

The term "allelic variant of a polymorphic region of an SR-BI gene" refers to a region of an SR-BI gene having one of several nucleotide sequences found in that region of the gene in a population of subjects. In certain embodiments, an "allelic variant of a polymorphic region of an SR-BI gene" may comprise a SNP within the SR-BI gene.

By "antibody" is meant a monoclonal or polyclonal antibody, e.g. an antibody that is specific for SR-BI or portions thereof. Such antibodies can be generated and tested by routine methods that are well known in the art.

By "low fertility" or "infertility" is meant inability to conceive a child by natural means, within a time period of between 6 months to 1 year of unprotected vaginal sexual intercourse.

By "decreased fetal viability" is meant the lack of fetal heartbeats.

The term "biological sample" or "sample" means biological material isolated from a subject. The biological sample may contain any biological material suitable for detecting the desired SNP, and may comprise cellular and/or non-cellular material from the subject. For example, a biological sample may be isolated from whole blood, plasma, serum, extracellular fluid, cytosolic fluid, tissue, solubilized cellular membrane samples, cultured cells, cell culture media, physiological buffers, combinations thereof, or other biological materials known in the art.

The terms "genetic predisposition," "genetic susceptibility," and "susceptibility" all refer to the likelihood that an individual subject will develop a particular disease, condition or disorder. For example, a subject with an increased susceptibility or predisposition will be more likely than average to develop a disease or condition, while a subject with a decreased predisposition will be less likely than average to develop the disease or condition. A genetic variant is associated with an altered susceptibility or predisposition if the allele frequency of the genetic variant in a population or subpopulation with a disease, condition or disorder varies from its allele frequency in the population without the disease, condition or disorder (control population) or a control sequence (wild type).

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide (e.g., a SNP), the identity of which differs in different alleles. A polymorphic region can also be several nucleotides long.

A "polymorphic gene" refers to a gene having at least one polymorphic region.

The terms "protein", "polypeptide" and "peptide" are used interchangeably herein when referring to a gene product.

By "increased probability" is meant at least a 10%, at least a 20%, at least a 30%, at least a 40%, at least a 50% or greater increase over a baseline probability. A baseline probability is, for example, the probability of a control subject having the indicated disease, disorder, or condition. For example, if the baseline probability is 5%, an increase of 10% means that the subject has a 5.5% probability of having or developing the condition. In particular embodiments of the present invention, the indicated condition may be infertility, decreased fetal viability in a pregnant female, recurrent spontaneous miscarriages/abortions or stillbirths, particularly a human female.

In particular embodiments of the invention, the methods and kits use probes or primers. Primers refer to nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes of the invention refer to nucleic acids which hybridize to the region of interest and which are not further extended. For example, a probe is a nucleic acid which hybridizes to a polymorphic region of an SR-BI gene, and which by hybridization or absence of hybridization to the DNA of a subject will be indicative of the identity of the allelic variant of the polymorphic region of the SR-BI gene. Probes or primers can be single stranded DNA (e.g., an oligonucleotide), double stranded DNA (e.g., double stranded oligonucleotide) or RNA.

Numerous procedures for determining the nucleotide sequence of a nucleic acid, or for determining the presence of mutations in nucleic acids include a nucleic acid amplification step, which can be carried out by, e.g., polymerase chain reaction (PCR). Accordingly, in one embodiment, the invention provides primers for amplifying a portion of the SR-BI gene comprising a polymorphic region of which specific allelic variants are associated with a particular disease or condition. In a preferred embodiment, the portion of the human SR-BI gene will be amplified to, e.g., detect which allelic variant of a polymorphic region is present in the SR-BI gene of a subject. Preferred primers comprise a nucleotide sequence complementary to an SR-BI intronic sequence or a specific allelic variant of a polymorphic region and of sufficient length to selectively hybridize with an SR-BI gene. In a preferred embodiment, the primer, e.g., a substantially purified oligonucleotide, comprises a region having a nucleotide sequence which hybridizes under stringent conditions to about 6, 8, 10, or 12, preferably 25, 30, 40, 50, or 75 consecutive nucleotides of an SR-BI gene.

Further details concerning probes and primers are well known in the art, and are also described in U.S. application Ser. No. 12/864,809, which is hereby incorporated by reference.

Materials and Methods

Materials.

Human lipoproteins (HDL and LDL) were purchased from Intracel, Inc. (Frederick Md., USA). Forskolin (Fo) was purchased from Sigma (Sigma-Aldrich Co., St. Louis, Mo., USA). MiniKit QIAmpDNA was obtained from Qiagen (Valencia, Calif.), and progesterone ELISA kit from ALPCO (Salem, N.H.). All other chemical reagents were purchased from Sigma.

Cell Culture.

HGL5 cells: HGL5 cells were purchased from Dr. Bnice Carr, University of Texas Southwestern. Cells were cultured in DMEM/F12 medium (Invitrogen, Carlsbad, Calif., USA) supplemented with 10% Ultra-low IgG FBS (Invitrogen), 1% ITS+premix (BD Biosciences, Bedford, Mass., USA), 100 U/ml penicillin, 100 µg/ml streptomycin and 1 µg/ml gentamicin (all from Invitrogen). Cells were plated in 12-well plates at density $1.4 \times 10^5$ cells/well for 2 hrs prior to transfection of oligonucleotides.

Primary Human Granulosa Cells:

Primary human granulosa cells were isolated from follicular fluid of two infertile women undergoing in vitro fertilization at the Johns Hopkins Greenspring Fertility Center. The study was approved by the Johns Hopkins Institutional Review Committee, and each subject signed a written consent form. Follicular fluid was centrifuged at 1500 rpm for 10 min, the pellet was re-suspended in 2 ml of sterile phosphate buffered saline (PBS) and the suspension was applied on top of 40% Percoll in PBS. After centrifugation at 3000 rpm for 30 min the granulosa cells were collected from the top of the Percoll gradient, washed 2 times with media and seeded for experiments in 12-well fibronectin-coated plates.

Knockdown of SR-BI and LDL Receptor (LDLR).

The siRNA duplexes and negative control duplex were purchased from Qiagen (Valencia, Calif., USA). Knockdown of each receptor was optimized by dose and time curves as recommended by the manufacturers' protocol and quantification of protein expression was determined by western blotting.

Cell Experiments.

Control cells were considered those incubated with scrambled oligonucleotides. Knockdown of the cells was carried out for 24-72 hours in complete medium as indicated above. Control medium was DMEM/F12 medium (without serum and supplements) containing dimethylsulfoxide (DMSO), the vehicle used to dissolve forskolin. The design of most of the experiments was to stimulate cells with control medium or the same medium containing Fo (10 µM), HDL (50 µg/ml), LDL (50 µg/ml), serum (10%), HDL+Fo, LDL+Fo, or serum+Fo for varying periods of time. The experiments were terminated by collecting the medium and subjecting it to centrifugation to pellet non-adherent cells. An aliquot of the medium was used for progesterone measurements using commercially available RIA kits. Cell lysates were harvested for western blotting, and total RNA was extracted for real-time PCR measurements.

Cholesteryl Ester Hydrolase Assays.

Cellular lipids were extracted with hexane-isopropanol (3:2) (i) and the distribution of intracellular esterified (EC) and unesterified (UC) cholesterol mass was measured by gas chromatography using stigmasterol as an internal control (ii). Cell proteins were measured using the BCA (bicinchoninic acid) method, and cholesterol mass values were normalized to mg cell protein.

Western Blotting.

Total cell lysates from cells were prepared using 5% SDS, 50 mM Tris-Cl, pH 7.6 buffer in the presence of protease inhibitor cocktail (1:100), phenylmethylsulfonylfluoride (1 mg/ml) and sodium orthovanadate (100 µM) (iii). Aliquots of the lysates (5 µg protein/lane) were subjected to SDS-PAGE in 10% gels and then transferred onto polyvinylidene fluoride membranes. Blots were blocked with 5% milk for 1 h, incubated with polyclonal anti-SR-BI (Novus) (1:1000) at 4° overnight, rinsed three times with TBS-0.1% Tween, reacted with anti-rabbit HR-peroxidase labeled IgG (Cell signaling) at room temperature for an additional hour, and then rinsed three more times with TBS-0.1% Tween. Bands were visualized using an Amersham ECL™ chemiluminescence kit (GE Healthcare), quantitated by densitometric scanning and normalized to β-actin expression.

Real Time PCR.

Aliquots of total RNA (50 ng) extracted from granulosa cells at different experimental conditions were reverse-transcribed in a reaction volume of 12 µl using 2.5 µM random hexamer, 500 µM dNTPs, 5.5 mM $MgCl_2$, 10 U ribonuclease inhibitor and 25 U MMLV reverse transcriptase. The reactions were carried out in thermal controller (50° C. for 60 min and 92° C. for 10 min). The resulting cDNAs were diluted with water. All probes and primers, including the internal control ribosomal protein L19 (RPL19) were synthesized by Applied Biosystems (Foster City, Calif.). The target gene and the RPL19 were detected in the same reaction. The PCR protocol consisted of 40 cycles of denaturing at 95° C. for 15 s and annealing/extending at 60° C. for 1 min per cycle. Detection of the gene expression was performed during the 2" step in a two step RT-PCR protocol. To quantify mRNA levels, a standard curve was constructed using pooled HGL5 cDNA generated from nontransfected cells. Data were analyzed as the inverse log([Ct-Y intercept]/slope of the standard curve) and expressed as a ratio of the target gene to endogenous control. (Fru K N, Vandevoort C A, Chaffin C L. Mineralocorticoid synthesis during the periovulatory interval in macaques. *Biol Reprod* 2006; 75:568-574.)

Primer and probe sequences are as follows: RPL19 forward: CCCCAATGAGACCAATGAAATC (SEQ ID NO:1); RPL19 reverse: CAGCCCATCTTTGATGAGCTT (SEQ ID NO:2); RPL19 probe: ATGCCAACTCCCGTCAGCAGATC (SEQ ID NO:3); 3βHSD forward: CCAGAACGGCCAC-GAAGA (SEQ ID NO:4); 3βHSD reverse: AGCTTTTTGCTGTACGGGTATG (SEQ ID NO:5); 3βHSD probe: AGCCTCTGGAAAACACATGGCCCA (SEQ ID NO:6) StAR forward: CCACCCCTAGCACGTG-GAT (SEQ ID NO:7); StAR reverse: TCCTGGTCACTGTA-GAGAGTCTCTTC (SEQ ID NO:8); StAR probe: CGGAGCTCTCTACTCGGTTCTC (SEQ ID NO:9); SCC forward: CTTCTTCGACCCGGAAAATTT (SEQ ID NO:10); SCC reverse: ATCCGCCGTCCCAGACA (SEQ ID NO:11); SCC probe: 6FAM-ACCCAACCCGATGGCT-GAGCAA (SEQ ID NO:12).

Progesterone Assays.

Progesterone levels in culture media were measured using commercially available radioimmunoassay kits (Siemens Healthcare Diagnostics Inc., Deerfield Ill.). The intra- and inter-assay variability was 4.1% and 5.2%, respectively.

Statistics.

Each experiment was performed using replicate wells, and each experiment was performed at least twice at different times. The data shown in the figures is expressed as the mean±standard error at each time point. Generalized linear mixed models were performed in order to account for the correlation among measurements within the experiment under exactly the same conditions, or over time, from the same cell. Statistical comparisons for treatment effects (such as scrambled versus SR-BI KD) and the treatment conditions (such as DMSO versus Fo) were evaluated with linear combinations of the estimates based on the mixed models. For the experiments with repeated measures taken over time from the same cell, linear combinations of the estimates based on the mixed models were also used to compare the mean changes between different time points for the combinations of treatment and incubating medium of interest. P values ≤0.05 were considered statistically significant. All analyses were performed using Stata 10.1 statistical software (StataCorp, College Station, Tex., 2009).

Study Demographics.

Granulosa cells were isolated from three hundred twenty women undergoing controlled ovarian hyperstimulation (COH) and IVF at The Johns Hopkins Fertility Center. The study design was previously reported (7). Access to lipid profiles or serum progesterone levels was not available, as these were not routinely ascertained for each subject prior to initiation of the IVF protocol. Forty-six subjects were removed from the final analysis because 19 were normal healthy oocyte donors, and the remaining 29 subjects had multiple IVF treatments. Subjects provided informed written consent for the IVF treatment and use of biological samples for genetic testing. The study was approved by the Johns Hopkins Institutional Review Board.

Granulosa Cell Retrieval and Isolation.

Follicular aspirates from each subject were centrifuged at 1500 g for 10 min at 4° C. (7). Follicular fluid was then collected and an aliquot was extracted for progesterone measurement. The cell pellet was re-suspended in phosphate-buffered saline (PBS), overlaid onto 40% (v/v) Percoll solution and centrifuged at 2500 g at 4° C. Granulosa cells at the Percoll-PBS interface were aspirated, re-suspended in PBS and pelleted by centrifugation at 1500 g. This step was repeated two times and the recovered cells were processed for genomic DNA extraction.

Clinical Fertility Measurements.

Subjects underwent COH and oocyte aspiration as previously described (7). Embryo transfers were performed on day 3 or 5 after retrieval. Intramuscular progesterone (50 mg daily) or vaginal progesterone (100 mg three times daily) were initiated the day following oocyte retrieval for luteal phase support. A serum pregnancy test was performed 14 days after embryo transfer by measuring serum hCG. Clinical pregnancy was defined as the presence of a gestational sac(s) and the data was coded as categorical '0=no' for no gestational sac(s) and '1=yes' for the presence of gestational sac(s). Patients were followed by transvaginal ultrasound until the detection of fetal heart motion (day 42 post-embryo transfer) and the data was coded as categorical '0=no' for heartbeat(s) and '1=yes' for heartbeat(s).

Follicular Fluid Analyses.

Progesterone levels were measured in follicular fluid extracts. The rationale for measurement of progesterone in follicular fluid was based on its availability and the direct contribution of ovarian progesterone secretion in the follicular fluid. One hundred microliters of follicular fluid were placed into a glass tube and 1 ml of petroleum ether was added (15). The tube was subjected to vortexing for 30 sec at maximum speed to separate the organic and inorganic phases. The organic phase was transferred into a new glass tube and the solvent evaporated under a stream of $N_2$. The residue was dissolved in PBS and analyzed by ELISA using a commercially available kit. The intra-assay and inter-assay coefficient of variation for the assay is 7.3% and 11.3%, respectively.

DNA Sequencing.

Genomic DNA was extracted from granulosa cells using a QIAamp DNA Mini Kit. The following SCARB1 SNPs (gene location) were characterized by direct sequencing in both directions of PCR products as previously described (16): rs4238001 (exon 1), rs10846744 (intron 1), rs5891 (exon 3), rs2278986 (intron 3), and rs5888 (exon 8). Sequence comparisons were determined using the Sequencher Program v.4.0 (Gene Code). The primer sequences and PCR conditions are available from the authors upon request. The rationale for selecting these particular SNPs was based on previously reported significant associations of these SNPs with phenotypic traits (17,18,19,20,21,22,23).

Statistical Analysis.

The differences in SCARB1 genotype frequencies across the racial/ethnic groups and the association of SCARB1 SNPs with clinical fertility measurements were measured by chi-square analysis. The association of SCARB1 SNPs with follicular progesterone levels was performed using one-way ANOVA. Each SCARB1 SNP was added to the multivariate stepwise regression analyses individually and together to assess whether the SNPs were independent predictors of follicular progesterone levels. Threshold significance values for selection and retention in the stepwise analysis were 0.25 and 0.10, respectively. All analyses were performed using JMP Genomics 4.2 (SAS Institute, Cary N.C.). Probability values <0.05 were considered statistically significant.

EXAMPLE 1

The object of this study was to knockdown SR-BI protein expression in HGL5 cells by incubating cells with SR-BI specific siRNA oligonucleotides (0-10 nM) for varying periods of time (24-72 h). As shown in FIG. 1A, SR-BI protein expression was markedly lower, in a dose- and time-dependent manner as compared with cells transfected with scrambled siRNA. SR-BI protein expression was maximally reduced (97%) in cells transfected for 72 h with 10 nM SR-BI siRNA. The western blot is representative of at least three independent experiments. Moreover, cell viability was comparable between the two experimental conditions, indicating that deficiency of SR-BI protein did not adversely affect cells (data not shown).

EXAMPLE 2

The object in this example was to determine whether there was a differential effect of HDL or LDL on steroidogenesis in control or SR-BI KD cells. HGL5 cells were first transfected with either scrambled siRNA (10 nM) or SR-BI siRNA (10 nM) for 72 h; the medium was aspirated and then cells were incubated with DMSO or the same medium containing either Fo (10 human serum (10%), HDL (50 protein/ml), LDL (50 µg protein/14 Fo+serum, Fo+HDL, or Fo+LDL for an additional 24 h. In scrambled cells, progesterone secretion was significantly higher in cells incubated with Fo alone (>2-fold, p<0.001), Fo+serum (>11-fold, p<0.001), Fo+HDL (>4.5 fold, p<0.001), Fo+LDL (>6-fold, p<0.001), serum alone (>3-fold, p<0.001), LDL alone (>3-fold, p<0.001), and HDL alone (>1.4-fold, p<0.001) as compared with DMSO (FIG.

1B). As compared to scrambled cells, progesterone secretion in SR-BI KD cells was significantly lower in all conditions ($p<0.01$).

EXAMPLE 3

Figure 2A:
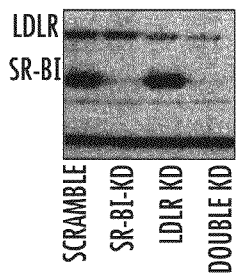
FIG. 2. The effect of LDL receptor (LDLR) and SR-BI KD in HGL5 cells. Panel A: Cells were transfected for 72 h with specific siRNA for either scrambled, SR-BI, LDLR, or both (double KD). Protein expression was determined by western blot. Each condition was performed in duplicate wells, and the western blot is representative of at least three independent experiments. Panels B-E. Progesterone secretion (ng/mg cell protein) was measured in scrambled (B), SR-BI KD (C), LDLR KD (D), or double KD (E) cells. Transfected cells were incubated in the presence of DMSO, Fo (10 µM), Fo+LDL (50 µg protein/rap, or LDL alone for an additional 6-24 h. Media levels of progesterone were measured by RIA. The data represent the mean±standard error of three independent experiments, with each experiment performed using duplicate wells. Error bars not visualized are contained with the symbol. Single asterisk denotes p<0.001 and double asterisk denotes p<0.05 as compared with scrambled cells.
Figure 2B:
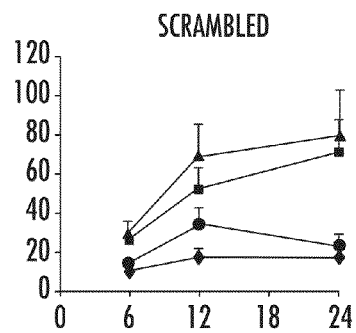
Figure 2C:
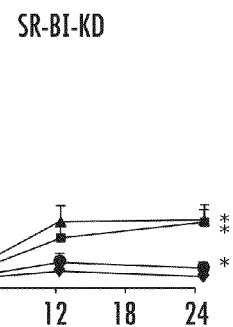
Figure 2D:
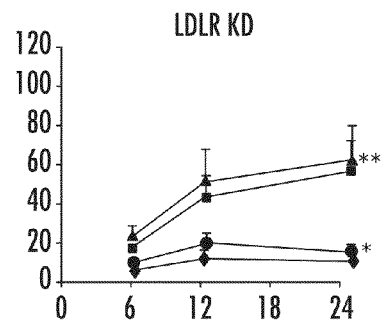
Figure 2E:
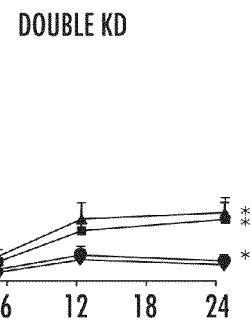

Having shown that knockdown of SR-BI significantly reduced progesterone secretion, the effects of LDLR KD alone and SR-BI-LDLR double KD on progesterone secretion were examined. Scrambled and receptor specific siRNA KD cells were incubated with control medium or the same medium plus Fo (10 µM), LDL (50 µg protein/ml), or Fo+LDL for varying periods of time (0-24 h). As shown in FIG. 2A, SR-BI, LDLR, and double KD protein levels were markedly reduced in the receptor specific KD cells as compared with scrambled cells (94%, 68%, 96[SR-BI]-86 [LDLR]%, respectively), although SR-BI KD appeared more efficient than LDLR KD. Scrambled and receptor specific siRNA KD cells were then incubated with control medium (DMSO) or the same medium plus Fo (10 µM), LDL (50 µg protein/ml), or Fo+LDL for 6-24 h. Cells were not incubated with HDL since this lipoprotein does not bind to the LDLR, but LDL does bind to SR-BI and the LDLR. Comparisons of the mean change of progesterone levels over time in the different receptor specific KD conditions (panels 2C-E) were made to the control scrambled cells (panel 2B). Thus, the mean change in progesterone secretion over 6-24 h was significantly different in SR-BI KD cells (panel 2C) incubated with LDL (81% lower, $p<0.001$), Fo (52% lower, $p<0.001$), and Fo+LDL (60% lower, $p<0.001$). In LDLR KD cells (panel 2D), the mean change in progesterone secretion was significantly different in cells incubated with LDL (41% lower, $p<0.001$) and Fo+LDL (23% lower, $p<0.05$), but not significantly lower in cells incubated with DMSO or Fo alone. In double KD cells (panel 2E), the mean change in progesterone secretion was significantly different in cells incubated with LDL (81% lower, $p<0.001$), Fo (70% lower, $p<0.001$), and Fo+LDL (66% lower, $p<0.001$).

EXAMPLE 4

Figure 3:
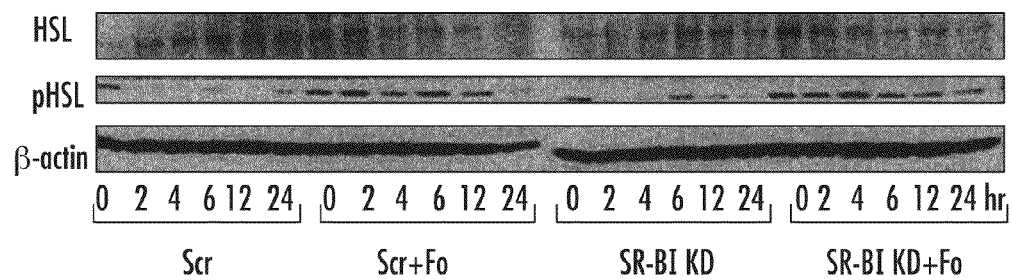
FIG. 3. Total and phosphorylated hormone sensitive lipase (HSL) expression in SR-BI KD cells. HGL5 cells were transfected with scrambled or SR-BI siRNA oligonucleotides for 72 h, and then transfected cells were incubated with DMSO or Fo (10 μM) for an additional 0-24 h. Cell lysates were harvested at each time point, and then total HSL and phosphorylated HSL (pHSL) were measured by western blotting using specific monoclonal antibodies. The blot is representative of three independent experiments.
Figure 4:
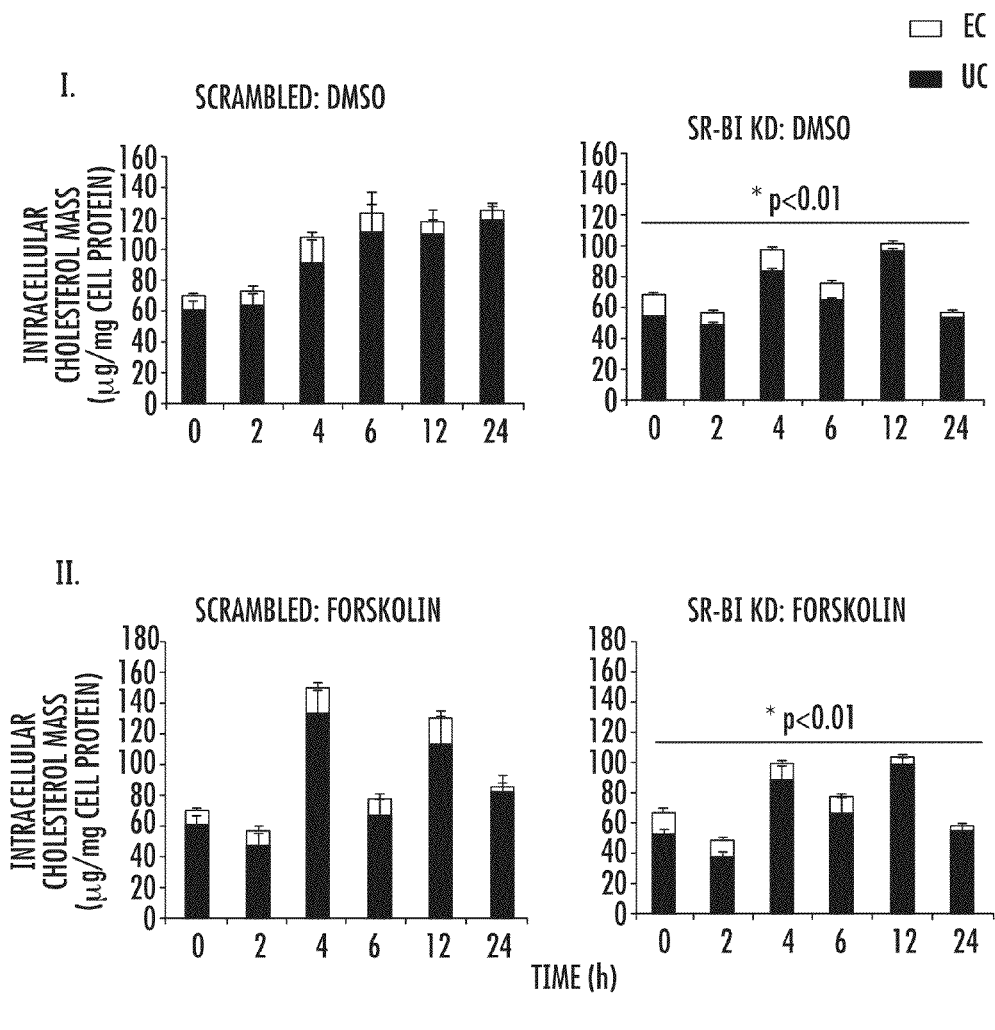
FIG. 4. Intracellular cholesterol mass in SR-BI KD cells under basal and forskolin stimulated conditions. Scrambled and SR-BI KD cells were incubated with DMSO or Fo (10 μM) for 0-24 h. At each time point intracellular lipids were extracted using hexane:isopropanol, then quantified by gas chromatography using stigmasterol as an internal standard, and normalized to mg cell protein. The data represent the mean±standard error of three independent experiments, with each experiment performed using triplicate wells. Asterisk denotes p<0.05 of the mean change of total cholesterol mass compared with scrambled cells. Cells designated '0 h' for DMSO or Fo were cells post-transfection and served as the baseline condition for the treatment phase. Error bars not visualized are contained with the symbol.
Figure 5:
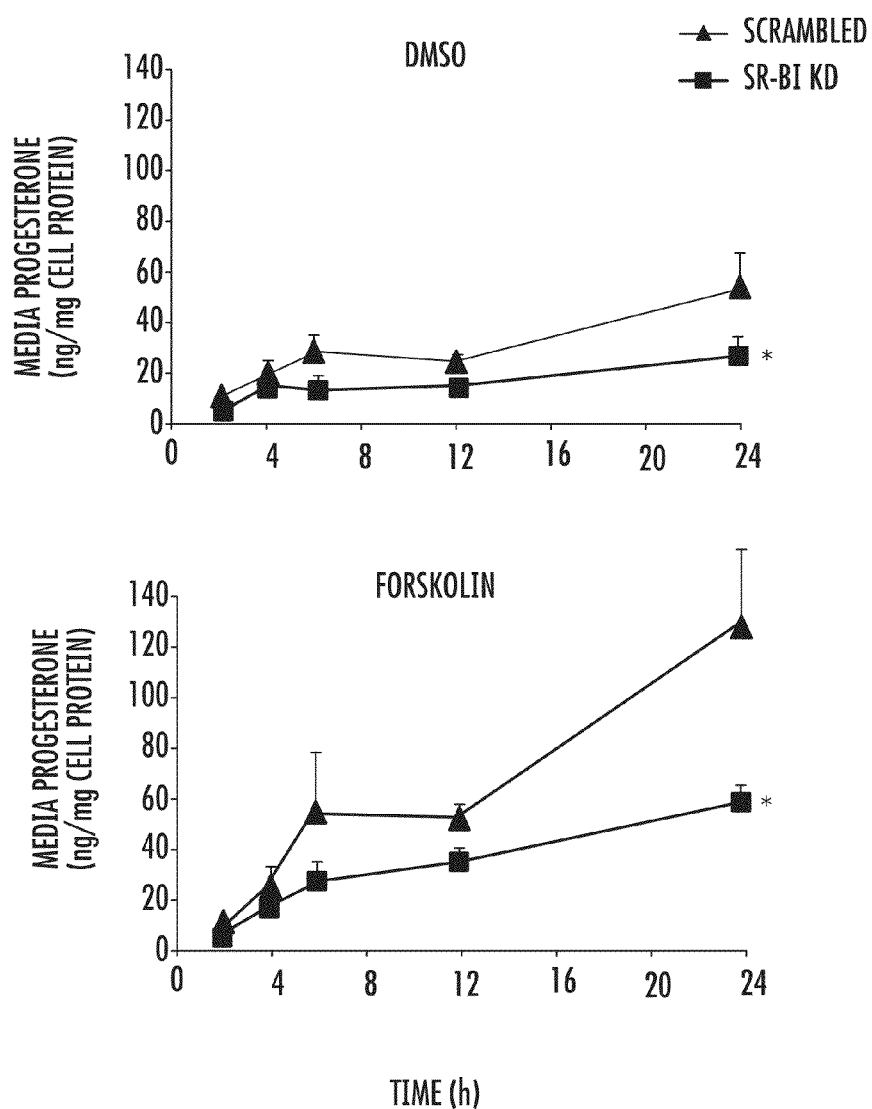
FIG. 5. Time course of progesterone secretion in SR-BI KD cells. Scrambled and SR-BI KD cells were incubated with DMSO or Fo (10 μM) for 2-24 h. Media progesterone levels were measured by RIA. The data represent the mean±standard error of three independent experiments, with each experiment performed using triplicate wells. Error bars not visualized are contained with the symbol. Asterisk denotes p<0.01 for the mean progesterone change over 2-24 h compared with scrambled cells.

What clearly emerged from the results shown in FIG. 2 was that SR-BI protein deficiency significantly reduced progesterone secretion. What also emerged was the effect of SR-BI KD on lipoprotein dependent (cells incubated with LDL) and lipoprotein independent (cells incubated with Fo alone without the presence of any lipoproteins in the culture media) progesterone secretion. The finding that SR-BI KD affected Fo-induced progesterone secretion was further investigated (especially given the findings of perinuclear localization of SR-BI without as of yet a defined function (2). A major effect of Fo is the phosphorylation of hormone sensitive lipase (pHSL), a key intracellular enzyme that stimulates CE hydrolysis with the generation of unesterified cholesterol (UC) needed for steroidogenesis (24). The effect of SR-BI KD on Fo stimulation on total and pHSL, intracellular cholesterol mass, and progesterone secretion was examined (FIGS. 3-5). Scrambled and SR-BI KD cells were incubated with either DMSO or Fo (10 µM) for varying periods of time (0-24 h). As shown in FIG. 3, in a representative western blot, pHSL expression increased over 2-4 h cells in both scrambled and SR-BI KD cells incubated with Fo as compared with DMSO. The expression of total HSL was also similar between scrambled and SR-BI KD cells. In FIG. 4 (panel I), over the entire 24 h period, the mean change in intracellular total cholesterol (TC) mass (esterified cholesterol [EC] plus UC) was significantly different between SR-BI KD cells incubated with DMSO as compared with scrambled cells ($p<0.05$), with the majority of the affect due to a reduction in UC mass in SR-BI KD cells after 12 h. In comparing the mean change in TC mass in cells incubated with Fo (panel II), we found significantly lower TC mass in SR-BI KD cells ($p<0.05$), with the majority of the affect due to a reduction in UC mass after 6 h. The corresponding progesterone levels are shown in FIG. 5, indicating significantly lower progesterone secretion in SR-BI KD cells incubated with DMSO over the 24 h time period ($p<0.01$), as well as significantly lower levels in SR-BI KD cells incubated with Fo ($p<0.01$).

EXAMPLE 5

Figure 6:
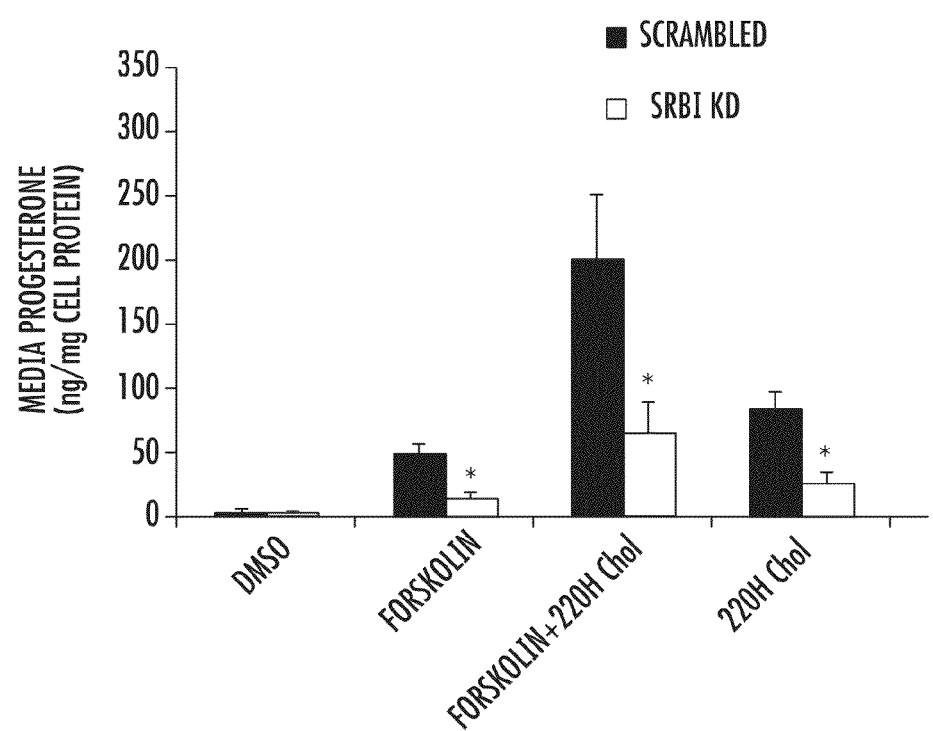
FIG. 6. The lack of effect of 22-hydroxycholesterol on progesterone secretion in SR-BI KD cells. HGL5 cells were transfected with scrambled or SR-BI siRNA for 72 h, and then incubated with DMSO, Fo (10 μM), Fo+22-OH cholesterol (20 μM), or 22-OH cholesterol for an additional 24 h. Media levels of progesterone were measured by RIA. The data represent the mean±standard error of three independent experiments, with each experiment performed using duplicate wells. Asterisk denotes p<0.001 compared with scrambled cells.
Figure 7:
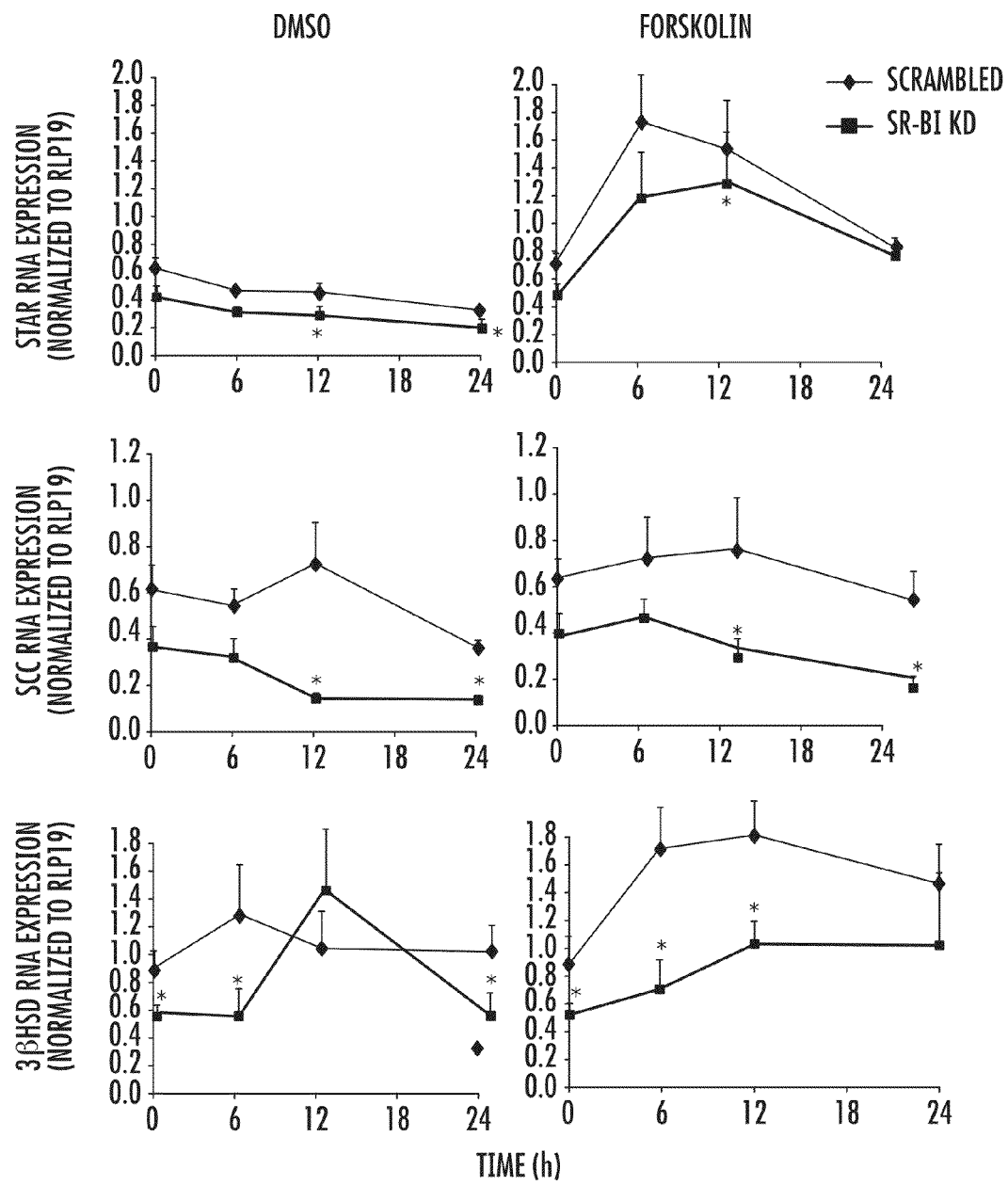
FIG. 7. Decreased RNA expression of StAR, SCC, and 3β-hydroxysteroid dehydrogenase in SR-BI KD cells. HGL5 cells were transfected with scrambled or SR-BI siRNA for 72 h, and then incubated with DMSO or Fo (10 μM) for varying periods of time (0-24 h). Total RNA was extracted at each time point and each gene target was measured by real-time PCR using RPL19 as the housekeeping gene. The data represent the mean±standard error of six independent experiments, with each experiment performed using duplicate wells The '0 h' time point reflects the baseline condition prior to the treatment phase with either DMSO or Fo. Asterisk denotes p<0.05 for the mean progesterone compared with scrambled cells.

Given that there was no available exogenous source of cholesterol in the culture media, the only other possible source of intracellular cholesterol available for progesterone synthesis would have been from de novo cholesterol synthesis. This suggested that SR-BI protein deficiency might be associated with impaired de novo cholesterol synthesis, and experiments were performed to determine if incubating cells with excess 22-OH cholesterol would overcome this possible impairment. Scrambled and SR-BI KD cells were incubated with DMSO, Fo (10 µM), 22-OH cholesterol (20 µM), or Fo+22-OH cholesterol for 0-24 h. As shown in FIG. 6, progesterone secretion was significantly lower in SR-BI KD cells incubated with either Fo ($p<0.001$), 22-OH cholesterol alone ($p<0.001$) or 22-OH plus forskolin ($p<0.001$) compared with scrambled cells. Similar results were observed in SR-BI KD primary granulosa cells isolated from two women undergoing oocyte retrievals (data not shown).

EXAMPLE 6

Results thus far show that SR-BI KD cells reduced progesterone secretion, and that the presence of excess 22-OH cholesterol did not overcome this impairment. Therefore it was logical to examine the effect of SR-BI deficiency on expression of factors in the steroidogenesis pathway downstream to HSL activation. Scrambled and SR-BI KD cells were incubated with DMSO or Fo (10 µM) for 0-24 hrs, and then total RNA was extracted from the cells. Baseline RNA expression of StAR and SCC were not significantly different from scrambled cells, whereas the baseline levels of 3βHSD RNA was significantly lower in SR-BI KD cells as compared with scrambled cells (FIG. 5) ($p<0.05$). Overall, mean RNA expression at varying time points for the three genes was significantly lower in SR-BI KD cells ($p<0.05$), regardless of treatment. In scrambled cells, the RNA expression of StAR and 3βHSD significantly increased in response to Fo stimulation, whereas the response of SCC and 3βHSD, in particular, in SR-BI KD cells to Fo was attenuated ($p<0.05$). In addition, it was found that intracellular levels of progesterone were significantly lower in SR-BI KD cells incubated with either DMSO or Fo as compared with scrambled cells (data not shown).

EXAMPLE 7

The studies in this example were carried out to evaluate the association of SCARB1 single nucleotide polymorphisms (SNPs) and fertility outcomes in women undergoing in vitro fertilization (IW). The study group consisted of 274 women (mean age of 36.4±4.6 years). The racial/ethnic composition was 55% Caucasian (n=152), 25% African-American (n=68), 12% Asian (n=34), 5% Hispanic, (n=14) and 2% other (n=6). Granulosa cells and follicular fluid were collected from women undergoing IVF. Five SCARB1 SNPs were sequenced and progesterone levels were measured in the follicular fluid. Fertility measurements were defined as the presence of gestational sac(s) and fetal heartbeat(s).

There was a significant difference in the genotype frequencies of the SCARB1 SNPs across the groups. In the Caucasian group, there was a significant association of carriers of the minor A allele of the rs4238001 SNP with lower follicular progesterone levels as compared with homozygous carriers of the major G allele (p=0.04). In this group, follicular progesterone levels were highly predictive of the rs4238001 SNP (p=0.03). In the entire cohort, minor allele carriers of rs4238001 did not have any viable fetuses at day 42 following embryo transfers (p=0.04). In the African-American group, there was an association between rs10846744 and gestational sac(s) (p=005), and fetal heartbeat(s) (p=0.004).

Figure 9:
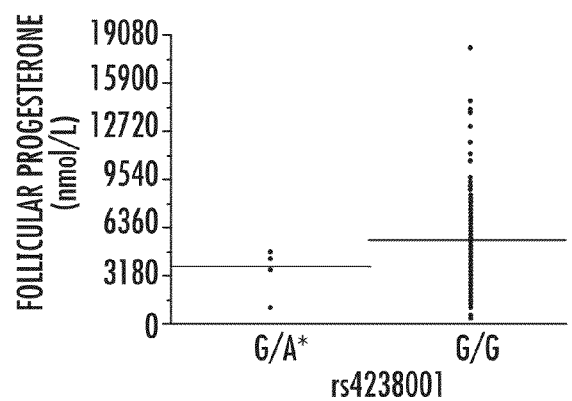
FIG. 9. Association of SCARB1 SNPs with Follicular Progesterone Levels: Caucasian Group. *p=0.04 as compared with homozygous major GG alleles by ANOVA analysis.

The gene location and genotype frequencies of the SCARB1 SNPs in this population are shown in Table 1.

gous carriers of the major allele (5629±253.8, 55% lower, p=0.04) (FIG. 9). In the African-American group, there were no significant associations of SCARB1 SNPs with follicular progesterone levels. The population size for Hispanics and Asian-Americans was too small for further sub-analysis, and these groups were not analyzed further.

Multivariate regression analysis was performed in the Caucasian group using age, BMI, baseline FSH levels, baseline LH levels, and in a stepwise fashion separately included each of the SCARB1 SNPs as independent covariates in the initial model, with follicular progesterone as the dependent variable. As shown in Table 2, following stepwise regression, only the rs4238001 SNP remained as an independent predictor of follicular progesterone levels (p=0.03).

TABLE 1

Gene location and genotype frequencies of SCAHB1 SNPs.

| Identification | Location | Amino acid change | Genotype Frequency (%) | | | | | | | | | | | | P values across all groups |
|---|---|---|---|---|---|---|---|---|---|---|---|---|---|---|---|
| | | | Caucasian | | | Hispanic | | | African American | | | Asian American | | | |
| | | | GG | GA | AA | GG | GA | AA | GG | GA | AA | GG | GA | AA | |
| rs4238001 G→A | exon 1 | yes | (97) | (3) | (0) | (100) | (0) | (0) | (93) | (7) | (0) | (97) | (3) | (0) | n.s. |
| rs10847644 C→G | intron 1 | no | CC (89) | CG (4) | GG (7) | CC (85) | CG (15) | GG (0) | CC (45) | CG (13) | GG (42) | CC (53) | CG (21) | GG (26) | <0.0001 |
| rs5891 G→A | exon 3 | yes | GG (98) | GA (1) | AA (1) | GG (100) | GA (0) | AA (0) | GG (99) | GA (1) | AA (0) | GG (100) | GA (0) | AA (0) | n.s. |
| rs2278986 T→C | intron 3 | no | TT (39) | TC (50) | CC (11) | TT (43) | TC (36) | CC (21) | TT (61) | TC (33) | CC (6) | TT (53) | TC (29) | CC (18) | 0.03 |
| rs5888 C→T | exon 8 | no | CC (39) | CT (51) | TT (17) | CC (29) | CT (50) | TT (21) | CC (54) | CT (37) | TT (10) | CC (38) | CT (50) | TT (12) | n.s. |

Significant differences between genotype frequencies of the rs10847644 (p<0.0001) and rs2278986 (p=0.03) were observed across all the racial/ethnic groups. No differences in the SCARB1 genotype frequencies between the Caucasian and Hispanic groups, nor between the African-American and Asian groups were observed. Significant differences in the rs10846744 (p<0.0001), rs2278986 (p=0.01), and rs5888 (p=01) genotypes were observed between the Caucasian and African-American groups. The genotype frequency of rs10847644 was significantly different between Caucasians and Asians (p<0.0001).

Figure 8A:
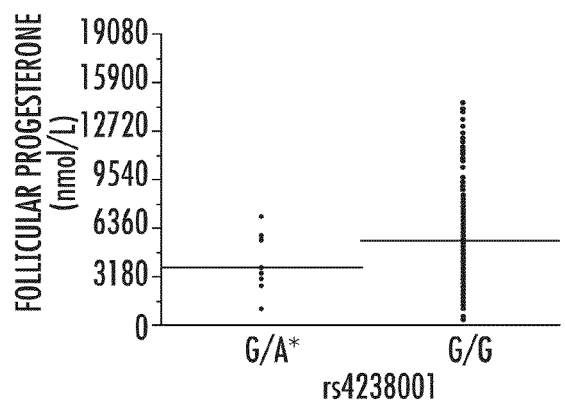
FIG. 8. Association of SCARB1 SNPs with Follicular Progesterone Levels: Entire Cohort. SCARB1 SNPs were genotyped by direct sequencing and follicular progesterone levels were measured in lipid extracts of follicular fluid using a commercially available assay. Panel A: *p<0.08 as compared with homozygous major G alleles by ANOVA analysis, Panel B: **p=0.03 compared with homozygous major C alleles.
Figure 8B:
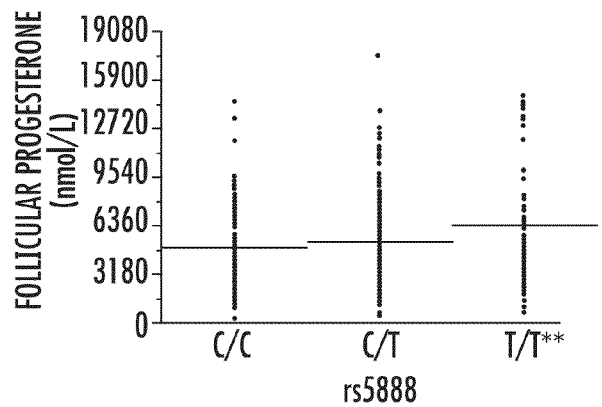

It was previously demonstrated by the inventor's research group that silencing SR-BI protein expression in immortalized human granulosa cells was associated with significantly lower progesterone secretion. Therefore, the univariate association of the SCARB1 SNPs with follicular progesterone levels was examined. As shown in FIG. 8A, for the entire group, carriers of the minor A allele for the rs4238001 SNP had lower follicular progesterone levels compared with carriers of the major G allele (29% lower, p<0.08). In contrast, it was found that subjects who were homozygous for the minor T allele of the rs5888 SNP had significantly higher follicular progesterone levels compared with subjects homozygous for the major C allele (homozygous major CC: 5061±284.9 nmol/L: heterozygous CT: 5367±260.1; homozygous minor TT: 6498±462.4) (p=0.03) (FIG. 8B). In the Caucasian group, carriers of the minor allele for rs4238001 had lower follicular progesterone levels (2528±1517) as compared with homozy-

TABLE 2

Multivariate regression analysis of the association of each SCARB1 SNP with follicular progesterone levels: Caucasian group.

A. Initial full model
Covariates: age (p = 0.35), BMI (p = 0.69), FSH (p = 0.34), LH (p = 0.65),
B. Final model with only rs4238001 included as SCARB1 SNP (p = 0.05, r = 0.20)
1. rs4238001    p = 0.03
2. age          p = 0.17

Figure 10:
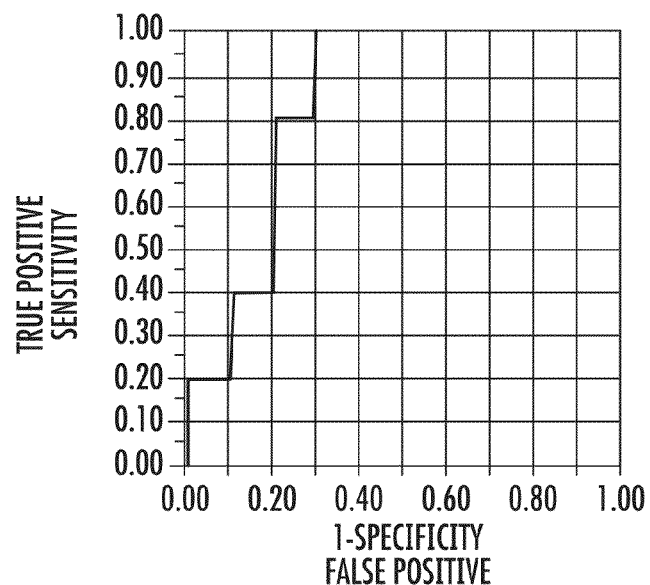
FIG. 10. Receiver Operator Characteristics Curve for prediction of rs4238001 minor allele based on follicular progesterone levels in the Caucasian group. Sensitivity 0.80, False positive rate 0.22, p=0.03.

Given that the rs4238001 remained as an independent predictor for follicular progesterone levels in the Caucasian group, we examined the sensitivity and specificity of follicular progesterone as a predictor of the rs4238001 SNP using the ROC analysis. As shown in FIG. 10, follicular progesterone was highly predictive with a sensitivity of 0.80 and a false positive rate of 0.22 (p=0.03).

Next, the association of each SNP with clinical fertility measurements, such as number of retrieved and fertilized oocytes, number of embryos transferred, clinical pregnancy, and fetal heartbeat(s) was examined. Of these measurements, for the entire cohort, a significant association was found between rs4238001 and heartbeat(s), with carriers of the minor A allele (n=9) not having any viable fetuses at day 42 post-embryo transfer (zero heartbeats) as compared with carriers homozygous for the major G alleles (n=63 with heartbeats, p=0.04, chi-square). A significant association was also observed between rs10846744 and the number of retrieved oocytes (homozygous major CC: 9.3±0.5; heterozygous CG: 10.4±1.7; homozygous minor GG: 12.3±1.1, p=0.05), clinical pregnancy (p=41.04, chi-square), and fetal heartbeats (p=0.03, chi-square).

In the Caucasian group, no significant association was seen between any of the SCARB1 SNPs and the clinical fertility parameters. However, in the African-American group, a significant association between rs10846744 and clinical pregnancy (p=0.006, chi-square), and fetal heartbeats (p=0.005, chi-square) was found.

DISCUSSION

The in vitro data presented herein is consistent with an adverse effect of SR-BI protein deficiency on progesterone levels. No changes in cell viability were observed despite the reduction in progesterone secretion. This might be because a complete loss of progesterone secretion in the SR-BI KD cells did not occur, as other investigators have found that complete loss of progesterone secretion in either monkey or rat granulosa cells was associated with increased atresia or apoptosis.

The results shown in FIG. 2 demonstrated that LDL cholesterol was more effective in inducing progesterone secretion compared to HDL, regardless of the presence or absence of SR-BI protein under basal or forskolin-stimulated conditions.

The results in FIG. 4 showed that LDLR deficiency can significantly reduce progesterone secretion, especially in cells incubated with LDL vs. Fo alone. It is possible that progesterone secretion in the presence of Fo alone might have been impaired if the LDLR had been more efficiently reduced. While not the main focus of the present investigation, it does not appear that knockdown of either SR-BI or LDLR affects the expression of the other.

A significant finding observed in FIG. 4 was the fact that progesterone secretion was significantly lower in SR-BI KD cells stimulated with Fo alone. It was not unexpected that progesterone secretion was lower in SR-BI KD cells incubated with LDL, given that a major function of SR-BI is mediating the uptake of neutral lipids from the core of lipoproteins, but it was surprising to observe that Fo only cells also showed significantly lower progesterone secretion. This finding prompted further investigation of the effects of SR-BI KD on progesterone secretion in an experimental model without the addition of lipoproteins in the culture media. With the knowledge that hydrolysis of stored cholesteryl esters would generate UC mass needed for newly synthesized progesterone, and that HSL has been shown to exert a major effect on CE hydrolysis, the effects of Fo on activation of HSL and intracellular cholesterol mass were evaluated in scrambled and SR-BI KD cells. The results shown in FIG. 5 demonstrated that Fo-stimulation induced phosphorylation of HSL in a time-dependent manner in both scrambled and SR-BI KD cells. These findings indicated that the protein kinase A pathway activated by Fo was intact in the SR-BI KD cells, suggesting that the impairment of progesterone secretion in SR-BI KD cells was likely downstream to phosphorylation of HSL. Scrambled and SR-BI KD cells were also incubated with dibutryl cAMP but this also did not overcome the defect in progesterone secretion, suggesting that the defect was downstream of HSL (data not shown).

A major function of pHSL in steroidogenic cells is the generation of UC mass from the hydrolysis of stored CEs. During the early time point significant differences were observed between TC mass changes in scrambled cells incubated with Fo as compared with cells incubated with DMSO. The changes in SR-BI KD cells was more subtle and only observed between 0-2 h. Over the 24 h time period, TC mass was significantly lower in SR-BI KD cells incubated with Fo as compared with scrambled cells. These observed differences in cellular TC mass correlated with the reduced progesterone secretion observed after 6 h (FIG. 6). Taken altogether, while it is possible that HSL was phosphorylated in SR-BI KD cells, its' activity might have nonetheless been impaired, preventing hydrolysis of stored CE as a source of cholesterol for progesterone secretion. However, failure of 22-OH cholesterol, with and without Fo, to overcome this impairment strongly suggested that deficiency of SR-BI was not negatively affecting HSL activity.

The lack of effect of 22-OH incubation on progesterone secretion in SR-BI KD cells also suggested that SR-BI deficiency was not negatively affecting de novo cholesterol synthesis. Moreover, if SR-BI deficiency was affecting intracellular cholesterol transport via StAR expression or function, incubating SR-BI KD cells with 22-OH cholesterol should have overcome this defect as well, as the effects of 22-OH cholesterol on progesterone secretion can be StAR independent. Therefore the effect of SR-BI deficiency on expression of SCC and 3βHSD was examined, and it was found that levels of RNA for these key enzymes was significantly lower in SR-BI KD cells.

Another significant finding in this study was the observation that SR-BI deficiency downregulated SCC and 3βHSD RNA expression, especially following Fo stimulation. It is unclear if there is a direct link between SR-BI expression and regulation of SCC and 3βHSD expression, but more than likely that an indirect link(s) explains this novel association. What is clear is that the association of SR-BI with StAR, SCC, and 3BHSD is independent of lipoproteins in the medium.

In these in vitro examples, the results have shown that SR-BI protein deficiency exerts a major influence on progesterone secretion in human granulosa cells. In addition to its well-known role of mediating uptake of neutral lipids from the core of lipoproteins, SR-BI appears to have a major influence on lipoprotein independent aspects of progesterone secretion, including regulating the expression of StAR, SCC and 3βHSD, key proteins involved in the steroidogenic pathway.

A major objective of the studies described herein was to determine the association of certain key SCARB1 SNPs with fertility measurements such as progesterone levels and measurements of embryo/fetal viability as little is known regarding the role of SCARB1 in human female reproductive physiology. The SCARB1 SNPs were selected based on prior investigations showing significant associations of these SNPs with cholesterol levels and subclinical atherosclerosis. The rationale for studying the association of SCARB1 SNPs with clinical fertility measurements in women undergoing IVF was due to the availability of granulosa cells and follicular fluid as by-products of oocyte retrievals.

The results show significantly lower follicular progesterone levels in women carriers of the minor A allele for rs4238001, especially in the Caucasian group (FIG. 9). The inventor recently identified a mechanism by which SR-BI protein deficiency would impair progesterone secretion in cultured human granulosa cells, reporting a novel, lipoprotein independent role of SR-BI deficiency in impairing de novo cholesterol synthesis, which led to downregulation of key steroidogenic enzymes such as P450 side-chain cleavage (P450 scc) and 3β-HSD (14 Komakova).

The rs4238001 SNP was significantly associated with lower follicular progesterone levels, and follicular progesterone levels were in turn highly sensitive and specific in predicting the presence of the SNP. This polymorphism is a nonsynonymous SNP that causes an amino acid change (glycine→serine) at position 2 in the SR-BI protein. The inventor with collaborators has previously shown that subjects with hyperalphalipoproteinemia (HALP, defined as having HDL cholesterol >60 mg/dl) and carriers of the minor A allele had 50% lower SR-BI protein levels as compared with homozygous carriers of the major G allele (22 West). The minor allele frequency (MAF) of this SNP in this HALP population was 12%, and in other populations as reported in dbSNP (website: ncbi.nlm.nih.gov/projects/SNP/snp_ref.cgi?rs=4238001) the frequency varies between 2-13%. Using an in vitro approach, they demonstrated that the rs4238001 SNP significantly increased SR-BI protein degradation; thus, this SNP is causal in inducing lower SR-BI protein expression. Therefore, the results in the current study of infertile women undergoing IVF showing an association of rs4238001 with lower follicular progesterone levels are consistent with the in vitro results of low SR-BI protein and low progesterone secretion, as well as the findings of significantly lower serum progesterone levels in SR-BI KO female mice. The ROC curve showed that follicular progesterone levels are highly predictive of SR-BI protein deficiency, strongly suggestive of the clinical utility of screening infertile women for SR-BI deficiency by genotyping for this particular SCARB1 SNP.

While we did not observe significant associations of SCARB1 SNPs with qualitative measurements of embryo viability (blastocyst number and grade) (data not shown), we did find significant association of rs4238001 and rs10846744 with quantitative fertility measurements. The association of rs4238001 with heartbeats was particularly compelling as carriers of the minor A allele had no viable fetuses at day 42 of pregnancy; this despite routine pharmacological progesterone supplementation to all subjects following embryo transfer. In rodents it has been observed that expression of P450 scc and 3β-HSD are significantly increased in endometrial glands at the time of implantation and this is associated with local progesterone production (26). SR-BI has also been shown to be expressed in human endometrial tissue and murine trophoblast giant cells (27-28). In human granulosa cells we have previously reported that silencing of SR-BI protein is associated with significantly reduced RNA expression of StAR, P450 scc, and 3βHSD (14). Moreover, Piccini et al. (29) has shown the importance of progesterone in acting as an immunosuppressant by activation of TH2 helper cells. Thus, it is plausible that deficiency of SR-BI in the human endometrium impairs local production of progesterone and thereby negatively affects fetal implantation and viability.

In conclusion, the results herein show that SR-BI exerts an independent effect on follicular progesterone levels, and follicular progesterone levels can be highly sensitive and specific predictors of rs4238001, and vice versa. Furthermore, this SNP and rs10846744 were also significantly associated with poor fetal viability, and this might be more dependent on endometrial progesterone production.

All patents and other references cited herein are hereby incorporated by reference.

REFERENCES (1) Acton S, Rigotti A, Landschulz K T, Xu S, Hobbs H H, Krieger M. Identification of scavenger receptor SR-BI as a high density lipoprotein receptor. *Science* 1996; 271:518-520.
(2) Ahras M, Naing T, McPherson R. Scavenger receptor class B type I localizes to a late endosomal compartment. *J Lipid Res* 2008; 49:1569-1576.
(3) Landschulz K T, Pathak R K, Rigotti A, Krieger M, Hobbs H. Regulation of scavenger receptor, class B, type I, a high density lipoprotein receptor, in liver and steroidogenic tissues of the rat. *J Clin Invest* 1996; 98:984-995.
(4) Trigatti B, Rayburn H, Vinals M, Braun A, Miettinen H, Penman M, Hertz M, Schrenzel M, Amigo L, Rigotti A, Krieger M. Influence of the high density lipoprotein receptor SR-BI on reproductive and cardiovascular pathophysiology. *Proc Natl Acad Sci USA* 1999; 96:9322-9327.
(5) Miettinen H E, Rayburn H, Krieger M. Abnormal lipoprotein metabolism and reversible female infertility in HDL receptor (SR-BI)-deficient mice. *J Clin Invest* 2001; 108:1717-1722.
(6) Yesilaltay A, Morales M G, Amigo L, Zanlungo S, Rigotti A, Karackattu S L, Donahee M H, Kozarsky K F, Krieger M. Effects of hepatic expression of the high-density lipoprotein receptor SR-BI on lipoprotein metabolism and female fertility. *Endocrinology* 2006; 147:1577-1588.
(7) Velasco M, Alexander C, King J, Zhao Y, Garcia J, Rodriguez A. Association of lower plasma estradiol levels and low expression of scavenger receptor class B type I in infertile women. *Fertil & Steril,* 2006; 85:1391-1397.
(8) Cherian-Shaw M, Puttabyatappa M, Greason E, Rodriguez A, VandeVoort C A, Chaffin C L. Expression of scavenger receptor-BI and low-density lipoprotein receptor and differential use of lipoproteins to support early steroidogenesis in luteinizing macaque granulosa cells. *Endocrinology* 2009; 150:957-965.
(9) Azhar S, Nomoto A, Leers-Sucheta S, Reaven E. Simultaneous induction of an HDL receptor protein (SR-BI) and the selective uptake of HDL-cholesteryl esters in a physiologically relevant steroidogenic cell model. *J Lipid Res* 1998; 39:1616-1628.
(10) Azhar S, Luo Y, Medicherla S, Reaven E. Upregulation of selective cholesteryl ester uptake pathway in mice with deletion of low-density lipoprotein receptor function. *J Cell Physiol* 1999; 180:190-202.
(11) Brannian J, Stouffer R. Native and modified (acetylated) low density lipoprotein-supported steroidogenesis by macaque granulosa cells collected before and after the ovulatory stimulus: correlation with fluorescent lipoprotein uptake. *Endocrinology* 1993; 132:591-597.
(12) Brannian J, Shiigi S, Stouffer R. Gonadotropin surge increases fluorescent-tagged low-density lipoprotein uptake by macaque granulosa cells from preovulatory follicles. *Biol Reprod* 1992; 47:355-360.
(13) Parinaud J, Perret B, Ribbes H, Chap H, Pontonnier G, Douste-Blazy L. High density lipoprotein and low density lipoprotein utilization by human granulosa cells for progesterone synthesis in serum-free culture: respective contributions of free and esterified cholesterol. *J Clin Endocrinol Metab* 1987; 64:409-17.
(14) Volpe A, Coukos G, Uccelli E, Droghini F, Adamo R, Artini P G. Follicular fluid lipoproteins in preovulatory period and their relationship with follicular maturation and progesterone production by human granulosa-luteal cells in vivo and in vitro. *J Endocrinol Invest* 1991; 14:737-42
(15) Plaino L, Stomati M, Casarosa E, Artini P G, Santuz M, D'Ambrogio G, Cobellis L, Luisi M, Genazzani A R, Petraglia F. Ovarian follicular fluid contains immunoreactive estriol: lack of correlation with estradiol concentrations. *Gynecol Endocrinol* 2000; 14:231-235.
(16) West M, Greason E, Kolmakova A, Jahangiri A, Asztalos B, Pollin T I, Rodriguez A. Scavenger receptor class B type I protein as an independent predictor of HDL cholesterol levels in subjects with hyperalphalipoproteinemia. *J Clin Endo Metab* 2009; 94:1451-1457.
(17) Acton S, Osgood D, Donoghue M, Corella D, Pocovi M, Cenarro A, Mozas P, Keilty J, Squazzo S, Woolf E A, Ordovas J M. Association of polymorphisms at the SR-BI gene locus with plasma lipid levels and body mass index in a white population. *Arterioscler Thromb Vasc Biol* 1999; 19:1734-1743.

(18) McCarthy J J, Lewitzky S, Reeves C, Permutt A, Glaser B, Groop L C, Lehner T, Meyer J M. Polymorphisms of the HDL receptor gene associated with HDL cholesterol levels in diabetic kindred from three populations. *Hum Hered.* 2003; 55:163-170.

(19) McCarthy J J, Lehner T, Reeves C, Molitemo D J, Newby L K, Rogers W J, Topol E F. Association of genetic variants in the I-IDL receptor, SR-BI, with abnormal lipids in women with coronary artery disease. *J Med Genet.* 2003; 40:453-458.

(20) Rodriguez-Esparragon F, Rodriguez-Perez J C, Hernandez-Trujillo Y, Macias-Reyes A, Medina A, Caballero A, Ferrario C M. Allelic variants of the human scavenger receptor class B type 1 and paraoxonase 1 on coronary heart disease: genotype-phenotype correlations. *Arterioscler Thromb Vasc Biol.* 2005; 25:854-860.

(21) Roberts C G P, Shen H, Mitchell B D, Damcott C M, Shuldiner A R, Rodriguez A. Variants in scavenger receptor class B type I gene are associated with HDL cholesterol levels in younger women. *Hum Hered* 2007; 64:107-113.

(22) McCarthy J J, Somji A, Weiss L A, Steffy B, Vega R, Barrett-Connor E, Talayera G, Glynne R. Polymorphisms of the scavenger receptor class B member 1 are associated with insulin resistance with evidence of gene by sex interaction. *J Clin Endocrinol Metab* 2009; 94:1789-1196.

(23) Naj A C, West M, Rich S S, Post W, Kao W H, Wasserman B A, Herrington D M, Rodriguez A. Association of scavenger receptor class B type I polymorphisms with subclinical atherosclerosis: the Multi-Ethnic Study of Atherosclerosis. *Circ Cardiovasc Genet* 2010; 3:47-52.

(24) Kraemer F B, Shen W-J, Harada K, Patel S, Osuga J-I, Ishibashi S, Azhar S. Hormone-sensitive lipase is required for high-density lipoprotein cholesteryl ester-supported adrenal steroidogenesis. *Mol Endo* 2004; 18:549-557.

(25) Trigatti B, Rigotti A. Scavenger receptor class B type I (SR-BI) and high-density lipoprotein metabolism: recent lesions from genetically manipulated mice. *Int J Tissue React* 2000; 22:29-37.

(26) Swarnakar S, Temel R E, Connelly M A, Azhar S, Williams D L. Scavenger receptor class B type I mediates selective uptake of low density lipoprotein cholesteryl ester. *J Biol Chem* 1999; 274:29733-29739.

(27) Rao R M, Jo Y, Leers-Sucheta S, Bose H S, Miller W L, Azhar S, Stocco D M. Differential regulation of steroid hormone biosynthesis in R2C and MA-10 Leydig tumor cells: role of SR-BI mediated selective cholesteryl ester transport. *Biol Reprod* 2003; 68:114-121.

I claim:

1. A method of identifying a female human subject at increased risk of low progesterone levels and/or poor fetal viability during pregnancy comprising:
   a. obtaining a biological sample from the female human subject;
   b. extracting genomic DNA from the biological sample;
   c. hybridizing primers to the genomic DNA to form a primer:DNA complex;
   d. amplifying the primer:DNA complex using polymerase chain reaction to amplify a portion of exon 1 of the SR-BI gene;
   e. sequencing the amplified DNA to detect the presence or absence of rs4238001 single nucleotide polymorphism (SNP);
   f. identifying the female human subject as having an increased risk of low progesterone levels and/or poor fetal viability during pregnancy based on the detection of an A allele at rs4238001 SNP; and
   g. treating the female human subject with progesterone.

2. A method of identifying a female human subject at increased risk of low progesterone levels and/or poor fetal viability during pregnancy comprising:
   a. obtaining a biological sample from the female human subject;
   b. extracting genomic DNA from the biological sample;
   c. contacting the genomic DNA with a probe that specifically hybridizes to a portion of exon 1 of the SR-BI gene comprising the rs4238001 SNP to form a probe:DNA complex, under conditions such that a probe:DNA complex would not form if the SNP was not present;
   d. identifying the female human subject as having an increased risk of low progesterone levels and/or poor fetal viability during pregnancy based on the detection of the probe:DNA complex as indicative of the presence of an A allele at rs4238001; and
   e. treating the female human subject with progesterone.

* * * * *